(12) United States Patent
Rinn

(10) Patent No.: US 6,813,948 B1
(45) Date of Patent: Nov. 9, 2004

(54) DEVICE FOR INVESTIGATING MATERIALS

(76) Inventor: Frank Rinn, Bierhelder Weg 20, D-69126 Heidelberg (DE)

(*) Notice: Subject to any disclaimer, the term of this patent is extended or adjusted under 35 U.S.C. 154(b) by 0 days.

(21) Appl. No.: 10/019,855

(22) PCT Filed: May 11, 2000

(86) PCT No.: PCT/DE00/01467

§ 371 (c)(1),
(2), (4) Date: Nov. 9, 2001

(87) PCT Pub. No.: WO00/68682

PCT Pub. Date: Nov. 16, 2000

(30) Foreign Application Priority Data

May 11, 1999 (DE) .......................................... 199 21 568

(51) Int. Cl.⁷ .............................................. G01N 29/04
(52) U.S. Cl. ............................... 73/584; 73/600; 73/602
(58) Field of Search .......................... 73/584, 579, 597, 73/598, 600, 602, 599

(56) References Cited

U.S. PATENT DOCUMENTS

| | | | |
|---|---|---|---|
| 3,292,143 A | 12/1966 | Russell | |
| 3,877,294 A | 4/1975 | Shaw | |
| 3,901,597 A | * 8/1975 | White | 356/4.05 |
| 4,926,691 A | 5/1990 | Franklin et al. | |
| 4,979,124 A | 12/1990 | Sachse et al. | |
| 5,060,516 A | * 10/1991 | Lau et al. | 73/602 |
| 5,621,172 A | 4/1997 | Wilson et al. | |
| 6,026,689 A | * 2/2000 | Snyder et al. | 73/602 |
| 6,053,052 A | * 4/2000 | Starostovic | 73/851 |
| 6,347,542 B1 | * 2/2002 | Larsson et al. | 73/12.12 |

FOREIGN PATENT DOCUMENTS

| | | |
|---|---|---|
| DE | 206 908 A | 2/1984 |
| EP | 0 448 896 A1 | 10/1991 |
| FR | 2 662 502 | 11/1991 |

* cited by examiner

Primary Examiner—Hezron Williams
Assistant Examiner—Jacques M. Saint-Surin
(74) Attorney, Agent, or Firm—Alston & Bird LLP

(57) ABSTRACT

A device for examining materials, in particular trees, other kinds of wood, and concrete, with a pulse generator (1) for generating a pulse that can be introduced into the material (2), with at least one sensor (3) adapted for being associated to the material (2) for detecting the pulse, and with an electronic evaluation device (4) for discriminating the pulse from interference pulses, is designed and constructed with respect to a universal application to even large test pieces of the material (2) being examined in such a manner that an electronic evaluation device (4) is associated to each sensor (3).

24 Claims, 2 Drawing Sheets

DEVICE FOR INVESTIGATING MATERIALS

BACKGROUND OF THE INVENTION

The invention relates to a device for examining materials, in particular trees, other kinds of wood, and concrete, with a pulse generator for generating a pulse that can be introduced into the material, with at least one sensor adapted for being associated to the material for detecting the pulse, and with an electronic evaluation device for discriminating the pulse from interfering pulses.

Devices for examining materials of the initially described kind are known from practice, and they exist in a large variety of types. They are, for example, devices, wherein the pulse time delay of shock waves is measured. From this pulse time delay, conclusions are drawn with respect to the quality of the material being examined. In the case of wood, for example, utility poles, the time delay of the shock waves correlates in the direction of growth or grain with the modulus of elasticity in the bending of wood, which enables an assessment of the load capacity, and the therefrom dependent categorization into quality classes. This influences the purchase price in the case of new poles.

In most cases, it is common to introduce into the material the shock wave or the pulse with a hammer serving as a pulse generator, either in a direct manner or via a screw or a bouncing pin. In the case of an axial irradiation of a pole by sound waves, the pulse is typically introduced at the front end. A sensor arranged at the other end of the material or pole detects the pulse that has been introduced into the material. A current pulse corresponding to this pulse is then guided from the sensor to a central electronic evaluation device, where the current pulse is analyzed by discriminating interfering pulses.

More specifically, an acceleration sensor in the pulse-generating hammer transmits in the instant of applying the stroke, the resultant current pulse via a line to a central electronic unit or electronic evaluation device, which analyzes the pulse, and starts a clock, depending on the result, namely a successful discrimination from, for example, interference vibrations. As soon as the sensor at the other end of the material or the other end of the measured length registers the arrival of the shock wave, it will likewise transmit a corresponding current pulse to the central electronic unit, which stops the clock, if the pulse meets the requirements with respect to intensity and length. Both the pulse from the hammer and the pulse from the sensor must each be electronically discriminated, i.e., be distinguished from other vibrations. This occurs each time in the central electronic evaluation device. For purposes of being able to distinguish between real pulses and spurious pulses, a user may normally adjust "gain" and "offset" in the central electronic evaluation device. From the time delay of the pulse and the distance between shock application and detector, it is possible to determine the pulse or shock velocity. Same allows to make statements as to the internal condition and the quality of the material being examined or the test piece, not only in the case of wood, but also in the case of concrete and other materials.

In the known device, the electronic signals of the acceleration sensors, the pulse generator, and the detectors, are transmitted via cables to a central electronic detection and evaluation device. This device also accommodates an accurate electronic clock. The discrimination and evaluation of the pulses, which were converted into electronic current pulses, previously introduced, and subsequently detected, thus occurs in a central location by means of corresponding electronic circuits. In this connection, the pulse shape is decisive for differentiating between real pulses and interference pulses. Thus, the pulse shape should not be altered or falsified on its way from the sensor through the cable to the electronic evaluation device, for example, by electromagnetic interferences or technical cable properties. To accomplish this, the transmission cables must be shielded and be of an extremely high quality, which leads to high prices, limited length of few meters, and restricted handling. Cables of this kind with a corresponding shielding react very sensitively to low temperatures and other external effects, so that they can be used only with limitations, and are very prone to interference. For example, for purposes of avoiding interferences, such cables should not extend in a loop. In particular, in the case of very long or large test pieces of the material being examined, it is not possible to use the known device, since there exist no adequately long cables, which enable an interference-free transmission of current pulses from the sensor or sensors to the central electronic evaluation device.

Consequently, the use of the known device for examining materials, in particular with respect to large test pieces, is very restricted on the materials being tested. A universal application of the known device is therefore not possible.

It is therefore an object of the present invention to describe a device for examining materials of the initially described kind, which enables a universal application with constructionally simple means, in particular also in the case of large test pieces of the material being examined.

SUMMARY OF THE INVENTION

The above and other objects and advantages of the present invention are achieved by a device of the type which is designed and constructed such that an electronic evaluation device is associated to each sensor.

According to the invention, it has first been recognized that the foregoing object is accomplished in a surprisingly simple manner alone because of a suitable arrangement of the electronic evaluation device. Furthermore, in accordance with the invention, a separate electronic evaluation device is associated for this purpose to each sensor. This association of respectively one electronic evaluation device to each sensor permits avoiding great cable lengths between the sensors and the electronic evaluation device, in particular with the use of a plurality of sensors. In comparison therewith, it is not possible to avoid in the case of most sensors, great cable lengths with the use of a central electronic evaluation device for all sensors in use, which are often arranged at great distances between one another.

The device of the present invention makes it now possible to perform the discrimination of pulses quasi directly on the sensors with minimal communication lengths. Since an electronic evaluation device is associated to each sensor, the spacings between the sensors are no longer important. Therefore, it would also be possible to arrange the sensors at a great distance between one another, while yet enabling a reliable discrimination of pulses.

Consequently, the device for examining materials according to the invention realizes a device, which permits a universal application with constructionally simple means, in particular also in the case of large test pieces of the material being examined.

As regards the kind of pulse, two alternatives present themselves. In this connection, the pulse could be a mechanical and/or an electrical pulse. A mechanical pulse is, for example, a shock wave, which is triggered, for example, by means of a hammer. However, it is also possible to introduce electrical pulses into the material being examined. In this instance, it is also possible to measure the time delay of the current pulse and/or its attenuation. The pulse may be a direct current or an alternating current pulse. In the case of the alternating current pulse, it is also possible to examine. its frequency response while passing through the material.

As regards a very short and reliable communication length between the sensor and the electronic evaluation device, the latter could be arranged directly adjacent to the sensor or be integrated in the sensor. In particular, the integrated arrangement of the electronic evaluation device in the sensor ensures a particularly compact and evaluation-reliable configuration of the device.

As regards a particularly simple processing of the measured data generated by the device, the electronic evaluation device could include a device for generating an electronic signal. In this instance, the electronic evaluation device could be designed such that the electronic signal is generated exactly at the moment, when a real measurement pulse is detected, which is discriminated from interference pulses. In the simplest case, the signal could be an electronic, preferably digital standard pulse. In this case, one has in mind in particular a TTL pulse.

It would be possible to transmit an electronic signal, which is generated by the electronic evaluation device, to a central unit, which preferably is, for example, a portable computer. In such a central unit, it would be possible to process the measured data in the form of, for example, time delays of the shock waves from the pulse input location to the respective sensor.

In particular with respect to a reliable transmission of the signal from the sensors or the electronic evaluation device to the central unit, it would be possible to interlink the sensors and/or electronic evaluation device electrically. For an electrical connection, one could use standard cables of the simplest kind, since it is not necessary to suppress here interferences or signal distortions. What matters is only a reliable transmission of an electronic standard signal. A costly discrimination in the central unit is no longer needed, since the decisive discrimination of real pulses from interference pulses already occurs in the electronic evaluation device. It would be possible to provide a closed-loop line or a star-shaped line. In this instance, it is necessary to accommodate the respective case of application. This means that in the case of large test pieces, a closed-loop line could be advantageous because of its shorter overall cable length as a whole.

As an alternative to a transmission via electrical lines, the transmission could occur by means of radio waves, ultrasonic waves, or infrared radiation. To this end, it would be possible to associate to each sensor a transmitter-receiver unit for radio waves, ultrasonic waves, or infrared radiation. Via such a transmitter-receiver unit, it would be possible to transmit especially the electronic signal of the electronic evaluation device, thereby avoiding extensive cabling.

In a concrete arrangement, one could associate a vibration detector to each sensor. The oscillation detector is used for detecting mechanical pulses. In a particularly simple manner, the oscillation detector could be a piezoelectric element.

For a reliable transmission of a mechanical and/or an electrical pulse from the test piece to the sensor, a transmission pin for the pulse could be associated to each sensor. In a constructionally very simple manner, the transmission pin could be a metal pin, preferably a steel pin. At the beginning of a measurement, such a transmission pin could be inserted into the test piece of the material being examined, whereupon the sensor is coupled with the transmission pin. In a particularly simple manner, the sensor could engage the transmission pin or suspend therefrom. If the material being examined consists, for example, of concrete, one could do without a transmission pin.

In the device for examining materials according to the invention, one measures, for example, the time delay of a pulse from a pulse input location to each individual sensor. In so doing, it is necessary to initialize the sensors. To this end, a clock could be associated to each sensor. For example, an initialization could occur in such a manner that the first sensor, which detects a real pulse, starts its clock and, in so doing, transmits at the same time a preferably electronic communication signal to the other sensors to reset their clocks to zero and to start them likewise. This initialization principle will be especially favorable, when the pulse is input or introduced in the direct vicinity of the first sensor.

Once a real pulse is detected, the electronic evaluation device transmits, for example, an electronic signal to a central unit. In this case, it is advantageous to associate to each sensor an individual identification means, so as to enable an allocation of the signals arriving at the central unit to the respectively transmitting sensor. To this end, the sensors could identify themselves by a clear code.

In a further advantageous manner, it would be possible to associate to each sensor a storage for measurement results, which enables a direct readout of the measurement results on each sensor.

Furthermore, it would be possible to associate to each sensor a display for the measurement results, which permits reading the measurement results directly on the sensor.

A particularly advantageous development of the device for examining materials could be provided with at least three sensors. This would permit generating last but not least three-dimensional graphs of the results with respect to the internal condition of the test piece. The more sensors are used, the more detailed will be such a graph. In this instance, it is essential that the sensors can be associated to the material in a geometrically independent relationship from one another. A rigid arrangement of the sensors, for example, in a closed-loop form is not necessary. For an effective evaluation of the three-dimensional measurement data, it is only necessary that the geometric positions of the sensors be determined.

With respect to a particularly elegant and practical introduction of pulses, the sensor or a plurality of sensors could be realized as pulse generators. To this end, it would be possible to associate to at least one sensor a device for introducing pulses. Such a device could be formed, for example, by a piezoelectric element, which serves at the same time as a vibration detector. As an alternative or in addition thereto, the device for introducing pulses could be a pin, preferably a metal pin. Such a pin could connect to the sensor via a coupling piece of rubber. For introducing pulses, the pin could be activated by means of a pulse generator in the form of a hammer.

As regards a reliable measurement of the pulses that are introduced by the pulse generator, it is essential that the introduced pulses be distinguished or discriminated from interference pulses. Interference pulses may be generated, for example, during the examination of a tree by automobiles passing by in a neighboring street. Even people walking by the test piece being examined may generate interference pulses above the ground or introduce them into the test piece. It will therefore be especially advantageous, when the sensors or electronic evaluation devices are able to recognize such interference pulses in each application individually already before the actual measurement. To this end, the electronic evaluation device could include means for self-calibration. In this case, the detection threshold of the electronic evaluation device itself is adjusted to a level, which is above the level of all previously detected interference pulses or interference vibrations. This self-calibration step could occur continuously, with a self-calibration being absent during the time of the actual measurement. With that, it is possible to suppress a substantial number of interference pulses right from the beginning.

As regards a simple determination of the positions of the sensors relative to one another, it would be possible to associate to the sensor or sensors pull-out measuring sticks. In the alternative, it would be possible to associate to the sensor or sensors a rope with an angle display. The rope interconnects adjacent sensors. As a result, it would be possible to determine the distance and angle from an adjacent sensor. With a known sensor size, it is possible to approximate from the sensor distances and angles of the rope connection, the geometry of the cross section of a sample in the tested region, for example, the cross section of a tree.

As an alternative or in addition thereto, it would be possible to provide an infrared or laser distance measuring instrument. In connection with the central unit, this would permit determining the position of the sensors and pulse input locations and displaying them as a three-dimensional image. In this case, it is possible to compute, display, and output a three-dimensional image of the internal condition directly from the determined pulse data.

For a better understanding of the teaching according to the invention, the essential aspects of the teaching according to the invention are explained one more time in the following:

To generate within the scope of the device according to the invention, three-dimensional graphs of a condition, at least three sensors, preferably of the same type are arranged in a desired geometry around the cross section or test piece being examined. In the case of standing trees, for example four to six sensors per cross section or stem section will suffice in most cases. The introduction of pulses may occur by means of a commercially available hammer. From the respective location of the pulse input, which occurs in different places, a corresponding measured value is obtained, which results after a corresponding processing of the measured value, in a three-dimensional, quasi tomographic cross sectional image. The pulse input may occur in any desired places of the test piece.

In a concrete realization, each sensor comprises its own, independent electronic control or electronic evaluation device, which includes, if need be, an electronic timer or a clock. After their conversion into current pulses, for example, via piezoelectric crystals, the mechanical or electrical pulses arriving from the test piece of the material being examined, are electronically processed and discriminated directly in the sensor. External interfering influences are thus directly suppressed in the sensor. With that, interferences, which have so far been problematic in the transmission system—cables—are precluded. Once a pulse arriving from the test piece is detected as correct, an electronic, preferably digital standard pulse, for example, TTL pulse will be generated. This pulse can be transmitted via simple, cost-favorable standard cables of an almost unrestricted length, or even via radio, infrared, or ultrasound, to other sensors or to a central unit. In this process, the sensors identify themselves by a clear code.

Optionally, the sensors are able to detect not only arriving pulses, but also generate and input themselves pulses, for example, via the reversed piezoelectric effect, inasmuch as, in principle, the same technology is therefor required.

For example, it is possible to interlink the sensors in the form of a closed-loop line. However, the data may also be transmitted in a star-shaped configuration, or via radio, to a central unit with a display, storage, and output, or directly to a preferably portable computer. In this arrangement, the number of sensors is quasi random. In an advantageous manner, each of these sensors identifies itself during the communication. It is necessary to identify the sensors only clearly and to allocate them in their position, to the position of the pulse input being registered during each pulse input.

In the case of trees, it may become necessary to arrange the sensors at a height of several meters. This may occur by means of telescopic rods, since the sensors may be either driven in directly or arranged on driven-in pins.

A typical measuring sequence or process could be performed as follows. First, one determines on the test piece the correct position of the sensors. Subsequently, for example, for examining trees or wood, the sensors are mounted, screwed, flanged, preferably to pins that are driven or screwed into the wood, so as to ensure an adequately stable connection with the wood. Furthermore, one determines, if necessary, the three-dimensional geometry of the test piece, which may occur in a laser and PC-assisted manner. Along with the determination of the geometry, the position of the sensors is determined. At the beginning of the measurement, all sensors are in a so-called "standby" position.

Depending on the task being posed, the introduction or input of pulses may occur in one location or in a plurality of locations of the test piece. Between the pulse input location and each sensor, this results in a measuring length with at least one individual measured value (for example, time delay, conductivity, damping). consequently, each pulse input results in a list of measured values for each sensor. These values are allocated to the respective length between the pulse input location and sensor.

In a simple embodiment, a bouncing pin that is secured, for example, with rubber, hangs above each sensor. Via this pin, it is possible to introduce shock waves, preferably with the use of a commercially available hammer.

In a second operation after positioning the sensors, at least one stroke is applied to the mounted pulse input pins. The advantage of this procedure lies in that the coordinates of the pulse input are each given by the coordinates of the sensors that are determined in any case.

However, the pulse input may also occur in any other locations, for example by means of a hammer and/or bouncing pin. For a direct assessment of internal wood damage, this procedure will already suffice, since the examining expert is able to determine and allocate the results directly. However, if it is intended to determine and display as much as possible a complete tomographic image, it will also be necessary to determine the respective position of the pulse input in a correspondingly exact manner.

The sensors are initialized either by the pulse input—via a cable connection between the hammer and sensors—or by a first sensor, which has identified an arriving pulse. Initialized sensors start their internal clocks and determine, for example the time frequency until they receive the next pulse. The transmission of the electronic standard pulses via cables or radio occurs almost at light speed, and thus is by an order of magnitude faster than the transmission of shock waves. As a result, the time delay by the electronic transmission of the initialization has no significant effect on the measuring accuracy.

Each sensor transmits the time between initialization and pulse detection to the other sensors and/or to the central unit, where the values are collected.

The results of the respective time delays are printed preferably directly on paper or shown on any portable, for example, watertight display.

The evaluation may be assisted by a computer, in that the display is connected to such a computer, or that direct use is made of a portable personal computer. The point of the shock wave input and sensor positions are entered either manually or graphically, or they automatically result from the fact that the sensor, next to which a stroke was applied, signals a zero time delay.

From the time delays of the respective connection segments between pulse input and sensor, quasi tomographic cross sectional images of the condition of the test piece result automatically. The number of connection segments and thus of the results is obtained as a function of the number n of the sensors, as follows:

If the pulse input does not directly occur on one of the sensors, n time delay results will be obtained per pulse, whereas n–1 results will be obtained, if the pulse is input directly on a sensor.

If the pulse is input on each sensor, n(n–1) results will be obtained. In the case of only six sensors, and thus six shock input points on one tree, thirty measuring segments are obtained with corresponding information about the delay time, which results in a quasi tomographic cross sectional image. Since only few seconds are needed per pulse input, it is possible to determine in this way in a very short time a comprehensive information about the internal condition.

For example, when two sensor rings are arranged at different heights on a standing tree, for example, at foot level and head level, one will automatically obtain comprehensive data about the condition of the entire volume between these two rings. From two rings with six sensors each, 12 pulse inputs—one each next to the sensor—result in a total of 132 connection segments with corresponding time delay information. From this, it is possible to compose a relatively accurate image of the condition of the wood.

The device of the present invention is not limited to a certain arrangement of the sensors—for example, around a cross section. Rather, it is possible to position the sensors freely. Likewise, since the number of sensors is not limited, it is thus also possible to determine the accuracy of the three-dimensional coverage of the test piece, since the accuracy is defined by the number and position of the sensors as well as the number of pulse inputs. An EDP-assisted coverage of the position of the sensors and pulse input, as well as a correspondingly automated evaluation enable an easy processing of the number of resulting values, which rapidly increases with the number of sensors. In this process it is necessary to determine or input only the geometry of the sample and the arrangement of the sensors.

The geometry or surface topology of the test piece and the position of the sensors are the basis of further evaluations. The accuracy of their coverage defines the accuracy and expressiveness of the results. This coverage may be sketchy or occur by means of commercially available distance measuring instruments. Likewise useful are laser distance measuring devices and position recording devices.

The device of the invention permits measuring the chronological and spatial intensity distribution of the pulses. In this connection, it is possible to input not only individual pulses and record their arrival, but also pulse sequences of identical or fluctuating intensity and frequency.

The electronic evaluation device comprises means for discriminating the pulse from interference pulses. In this connection, it would here be possible to integrate a corresponding software.

In a particularly advantageous manner, the device is made waterproof for outdoor use, thereby ensuring a long and troublefree operation of the device.

It would be possible to place the sensor not only on a pin, but also on a star-shaped pin combination, which includes pin tips pointing in different directions. When the arriving pulses are separately detected, each by the individual tip, it will be possible to determine results over the spatial direction of the pulses, which is very interesting in the case of trees, since there are different radial and tangential propagation responses.

The bouncing pin, which can be actuated either by a hammer or a sensor, may be oriented in a different direction. This permits taking into account a different propagation response in the material.

In the device of the present invention, a plurality of sensors enable quasi tomographic determinations of the internal condition with only few measurements. In this instance, identically adjusted sensors of only one kind are needed, which reduces the costs of manufacturing. The sensors evaluate pulses from the material being examined directly, independently, and thus "in situ", which reduces sources of interference and expense. For example, the shock input may occur by means of a commercially available hammer, which is very flexible and cost-favorable. The sensor connection requires only simple, commercially available, and cost-favorable connection cables, or it may occur via radio or other methods of remote transmission, since only electronic standard pulses are transmitted, which are insensitive to external interferences.

Based on the technical characteristics of the system, it is possible to position on the test piece, without limitation, any desired number of sensors. As a result of using a sensor shielding, standard cables, and transmitted pulses, the device is extremely insensitive to electromagnetic interference radiations, incorrect handling, mechanical loads, and other disturbances.

Quasi tomographic cross sectional images result in an automatic and a very simple way.

Volume-relevant results are obtained with the use of as few as three sensors. A plurality of sensors permits in a simple manner a three-dimensional coverage of the condition of almost any desired kind. A measurement can occur very rapidly by first inserting the pins, then mounting the sensors, and subsequently generating pulses by a shock or in any other fashion. Finally, the measurement results are noted or recorded. Only few minutes are needed for the therefor required two loops around the tree.

There exist various possibilities of improving and further developing the teaching of the present invention in an advantageous manner. To this end, reference may be made to the following description of an embodiment of the device according to the invention with reference to the drawing. In conjunction with the description of the preferred embodiment of the device according to the invention with reference to the drawings, also generally preferred improvements and further developments of the teaching are described.

DETAILED DESCRIPTION OF THE PREFERRED EMBODIMENT

Figure 1:
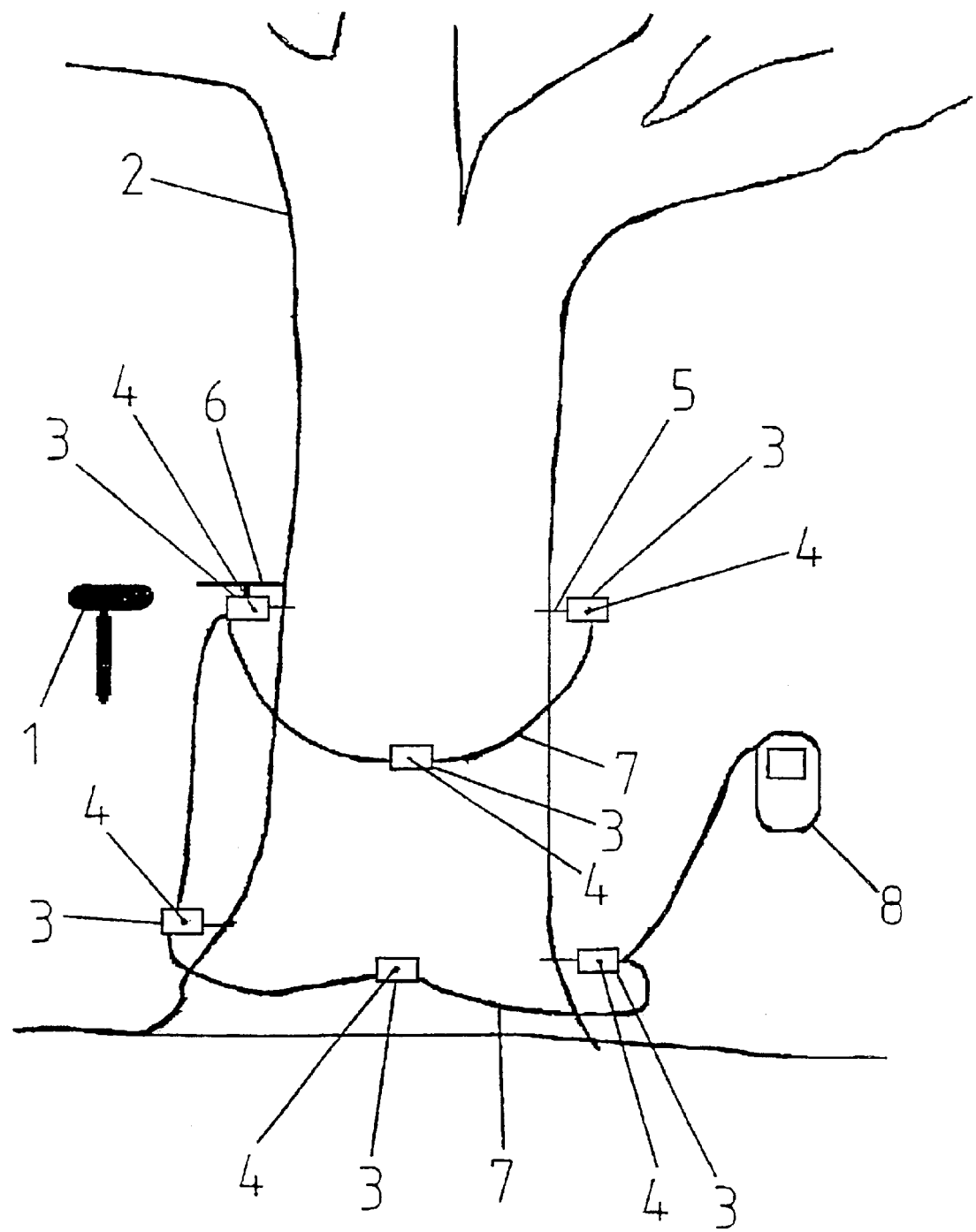
FIG. 1 is a schematic view of an embodiment of the device according to the invention for examining materials in a state arranged on a tree.

FIG. 1 is a schematic view of the embodiment of the device according to the invention for examining materials. The device comprises a pulse generator 1 for generating a pulse that can be introduced into a material 2. A tree is used as the material 2 being examined. Furthermore, the device includes six sensors 3 associated to the material 2 for detecting the pulse with six electronic evaluation devices 4 for discriminating the pulse from interference pulses. As regards a universal application of the device to even large test pieces, a separate electronic evaluation device 4 is associated to each sensor 3.

The electronic evaluation device 4 performs the discrimination of real introduced pulses from interference pulses. No long communication paths are needed between the sensor 3 or a vibration detector and the electronic evaluation device 4. In the illustrated embodiment, the electronic evaluation device 4 is integrated in the sensor 3. The sensors 3 are connected to the material 2 by means of a transmission pin 5. In this connection, the sensors 3 engage the transmission pin 5 or suspend therefrom. By way of example, a device for introducing pulses is associated to one of the sensors 3 in the form of a pin 6. The pulses are introduced by a stroke with the hammer on pin 6.

The sensors 3 are interlinked via connection cables 7. Furthermore, a connection is provided between the sensors 3 and a central unit 8. The central unit 8 receives electronic signals, which are generated by the electronic evaluation devices 4 of the respective sensors 3, when a real pulse is detected. In this process, an individual code is determined for each sensor 3, so that the central unit 8 is able to allocate the arrival location of the detected pulse.

Figure 2:
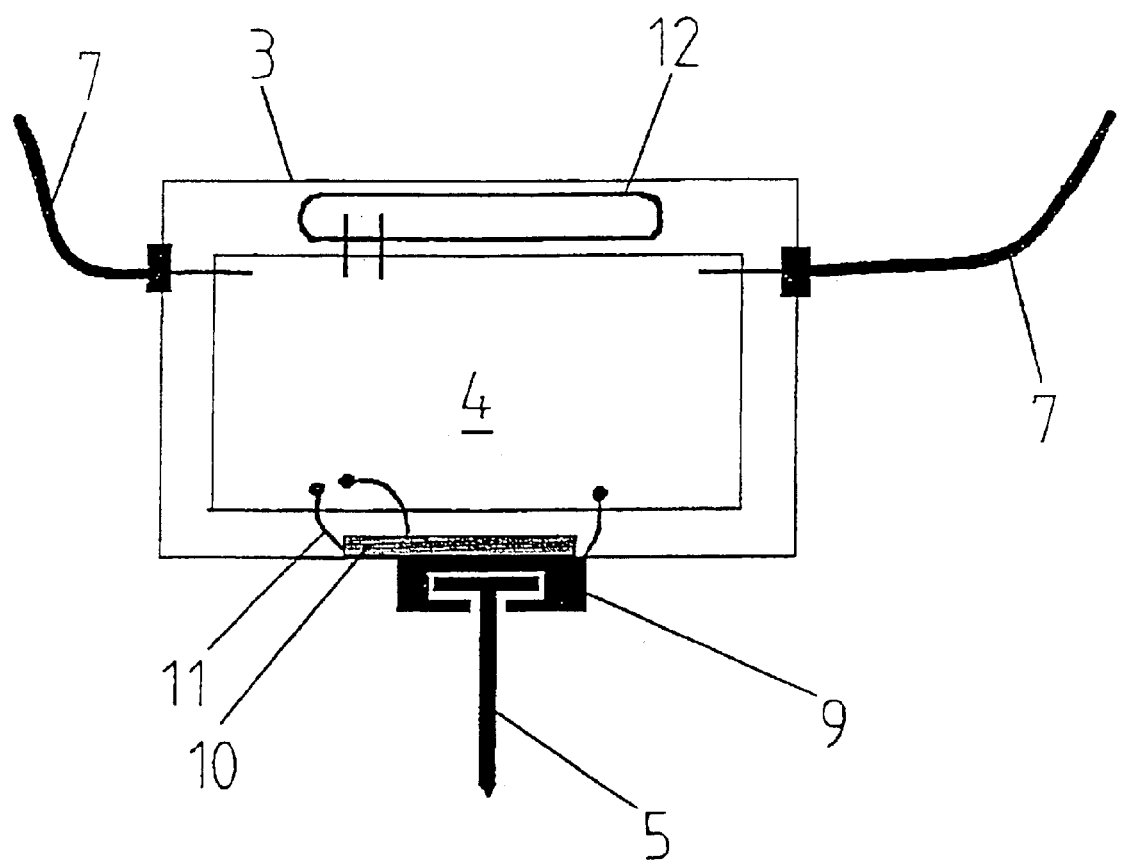
FIG. 2 is a schematic top view of a sensor of the embodiment of FIG. 1.

FIG. 2 is a schematic top view of a sensor 3 of the embodiment of FIG. 1. The sensor 3 includes an integrated electronic evaluation device 4. The pin 5 serving to connect to the material is coupled with the sensor 3 via a coupling piece 9. In direct connection with the coupling piece 9, a vibration detector 10 is provided, which is formed by a piezoelectric element. The electronic evaluation device 4 and the vibration detector 10 are coupled via an electric connection 11.

Both the transmission pin 5 and the coupling piece 9 may be made of a conductive material, preferably metal. This ensures not only a transmission of vibrations from the material 2 to the vibration detector 10, but also a transmission of electrical pulses to the vibration detector 10 and, thus, via the electrical connection 11, to the electronic evaluation device 4. With that, it is possible to detect with the sensor 3 not only mechanical, but also electrical pulses.

The transmission of an electronic signal, which is generated by a special device associated to the electronic evaluation device 4, or of other signals from the sensor 3 may occur as an alternative to the transmission via cables 7, via a transmitter-receiver unit 12 for radio waves, ultrasonic waves, or infrared radiation. The transmitter-receiver unit also permits an initialization of the sensors 3 at the beginning of a measurement. In this case, the connection cables 7 may be omitted. The transmitter-receiver unit 12 may be used for transmitting all kinds of signals, measurement results, or the like.

The electronic evaluation device is used as an independent unit with a central processing unit.

As regards further advantageous developments of the device according to the invention for examining materials, the general part of the description as well as the attached claims are herewith incorporated by reference for purposes of avoiding repetitions.

Finally, it should be expressly pointed out that the above-described embodiment of the device according to the invention merely serves to describe in greater detail the claimed teaching, but without limiting it to this embodiment.

What is claimed is:

1. A device for examining materials comprising
   a pulse generator for generating a pulse that can be introduced into the material,
   at least one sensor configured for being positioned with respect to the material so as to detect the pulse, and
   an electronic evaluation device for discriminating the pulse from interfering pulses, with the electronic evaluation device and the at least one sensor being integrated in a unitary one-piece structure, whereby the pulse evaluation may be effected adjacent the sensor with minimal communication paths and minimal electromagnetic interference.

2. The device of claim 1 wherein the pulse is a mechanical and/or electrical pulse.

3. The device of claim 1 wherein the electronic evaluation device includes means for generating an electrical signal.

4. The device of claim 3 wherein the electrical signal is connected for transmission to a central unit.

5. The device of claim 4 wherein the central unit comprises a personal computer.

6. The device of claim 1, wherein said device comprises a plurality of said sensors, and wherein an electronic evaluation device is integrated with each sensor as part of a unitary structure.

7. The device of claim 6 wherein said sensors are electrically interconnected.

8. The device of claim 6 wherein each of the sensors is operatively connected to a central unit.

9. The device of claim 6 wherein each of the sensors is operatively connected to a central unit via a transmitter-receiver unit associated with each sensor.

10. The device of claim 6 wherein each of the sensors has a vibration damper associated therewith.

11. The device of claim 10 wherein each vibration damper is a piezoelectric element.

12. The device of claim 6 wherein a transmission pin for detecting the pulse is associated with each sensor.

13. The device of claim 6 wherein a clock is associated with each sensor.

14. The device of claim 6 wherein an identification symbol is associated with each sensor.

15. The device of claim 6 wherein a storage for measurement results is associated with each sensor.

16. The device of claim 6 wherein a display for measurement results is associated with each sensor.

17. The device of claim 6 wherein said pulse generator comprises means for introducing electrical pulses into the material being examined.

18. The device of claim 6 wherein said pulse generator is mounted to at least one of said unitary structures for introducing pulses to the material being examined.

19. The device of claim 18 wherein said pulse generator includes a pin.

20. The device of claim 6 wherein said pulse generator comprises a hammer.

21. The device of claim 6 wherein each electronic evaluation device includes means for self calibration.

22. The device of claim 6 wherein each sensor is connected to a pull out measurement stick.

23. The device of claim 6 wherein each sensor is connected to a rope with an angle display.

24. The device of claim 6 further comprising an infrared or laser distance measuring instrument for measuring the position of each sensor.

* * * * *